(12) United States Patent
Koester et al.

(10) Patent No.: US 9,174,047 B2
(45) Date of Patent: Nov. 3, 2015

(54) ELECTRICAL FEEDTHROUGH ASSEMBLY

(75) Inventors: Kurt J. Koester, Los Angeles, CA (US); Chuladatta Thenuwara, Castaic, CA (US); Timothy Beerling, San Francisco, CA (US); Mark B. Downing, Valencia, CA (US); David Stuursma, Castaic, CA (US); Logan Palmer, Santa Monica, CA (US)

(73) Assignee: ADVANCED BIONICS AG, Staefa (CH)

( * ) Notice: Subject to any disclaimer, the term of this patent is extended or adjusted under 35 U.S.C. 154(b) by 347 days.

(21) Appl. No.: 13/643,992

(22) PCT Filed: May 10, 2011

(86) PCT No.: PCT/US2011/035986
§ 371 (c)(1),
(2), (4) Date: Jan. 8, 2013

(87) PCT Pub. No.: WO2011/143266
PCT Pub. Date: Nov. 17, 2011

(65) Prior Publication Data
US 2013/0100595 A1   Apr. 25, 2013

Related U.S. Application Data

(60) Provisional application No. 61/333,856, filed on May 12, 2010.

(51) Int. Cl.
*A61N 1/36* (2006.01)
*A61N 1/375* (2006.01)
(Continued)

(52) U.S. Cl.
CPC .......... *A61N 1/36032* (2013.01); *A61N 1/3754* (2013.01); *H01L 23/045* (2013.01);
(Continued)

(58) Field of Classification Search
USPC ......................................................... 439/589
See application file for complete search history.

(56) References Cited

U.S. PATENT DOCUMENTS 3,302,961 A   2/1967   Franklin
5,033,666 A * 7/1991   Keusseyan et al. ........ 228/122.1
(Continued)

FOREIGN PATENT DOCUMENTS

EP   0488193 A1   6/1992
WO   97/38752     10/1997
(Continued)

OTHER PUBLICATIONS

Schwartz; The ASM Handbook: Brazing; 2nd Edition; 2002; pages: Title page, copyright page, Chapters 1-13, pp. 119-122, 313-319 and 329-333.
(Continued)

*Primary Examiner* — Timothy Thompson
*Assistant Examiner* — Krystal Robinson
(74) *Attorney, Agent, or Firm* — Steven L. Nichols; Van Cott, Bagley, Cornwall & McCarthy P.C.

(57) ABSTRACT

A device includes a hermetically sealed case with electronic circuitry housed within. One surface of the hermetically sealed case includes a metallic plate and a co-fired ceramic electrical feedthrough with a number of vias. The co-fired ceramic electrical feedthrough is hermetically joined to the metallic plate and a hybrid circuit is connected to the feedthrough.

22 Claims, 10 Drawing Sheets (51) Int. Cl.
*H01L 23/045* (2006.01)
*H01L 25/16* (2006.01)
*H01R 43/00* (2006.01)
*H05K 5/00* (2006.01)
*H01L 23/498* (2006.01)

(52) U.S. Cl.
CPC ............ *H01L 25/16* (2013.01); *H01R 43/005* (2013.01); *H05K 5/0095* (2013.01); *H01L 23/49827* (2013.01); *H01L 2924/0002* (2013.01); *H01L 2924/09701* (2013.01); *Y10T 29/49204* (2015.01)

(56) References Cited

U.S. PATENT DOCUMENTS

| | | | |
|---|---|---|---|
| 5,276,963 A | | 1/1994 | Flanders |
| 5,683,435 A | * | 11/1997 | Truex et al. ............... 607/37 |
| 6,165,820 A | | 12/2000 | Pace |
| 6,414,835 B1 | * | 7/2002 | Wolf et al. ............... 361/302 |
| 7,068,491 B1 | * | 6/2006 | Burdon et al. ............ 361/313 |
| 8,277,227 B2 | | 10/2012 | Darley et al. |
| 2002/0139556 A1 | * | 10/2002 | Ok et al. ................. 174/50.6 |
| 2006/0247734 A1 | | 11/2006 | Greenberg et al. |
| 2009/0124965 A1 | * | 5/2009 | Greenberg et al. ........... 604/67 |

FOREIGN PATENT DOCUMENTS

| | | | |
|---|---|---|---|
| WO | 9738752 A2 | | 10/1997 |
| WO | WO 9738752 A2 | * | 10/1997 |
| WO | 2007035299 A1 | | 3/2007 |
| WO | 2009/018172 A2 | | 2/2009 |

OTHER PUBLICATIONS

Clauser; The Encyclopedia of Engineering Materials and Processes; pages: Title page, copyright page, pp. 131-133; 1963.

Pecht; Handbook of Electronic Package Design; Title page, copyright page, pp. 93-97, 101, 115-116, 121-148, 202-210, 801, 803, 834; Aug. 1991.

Brigham Young University; Coefficient of Thermal Expansion (CTE); http://www.cleanroom.byu.edu/CTE_materials.phtml; p. 1, 1994.

Rice University; http://www.owlnet.rice.edu/~msci301/ThermalExpansion.pdf; Thermal Expansion; Chapter 2; pp. 9-16; 2004.

* cited by examiner

ELECTRICAL FEEDTHROUGH ASSEMBLY

RELATED DOCUMENTS

The present application claims the benefit under 35 U.S.C. §119(e) of U.S. Provisional Application No. 61/333,856, entitled "Electrical Feedthrough Assembly" filed May 12, 2010, which application is incorporated herein by reference in its entirety.

BACKGROUND

In human hearing, hair cells in the cochlea respond to sound waves and produce corresponding auditory nerve impulses. These nerve impulses are then conducted to the brain and perceived as sound.

Damage to the hair cells results in loss of hearing because sound energy which is received by the cochlea is not transduced into auditory nerve impulses. This type of hearing loss is called sensorineural deafness. To overcome sensorineural deafness, cochlear implant systems, or cochlear prostheses, have been developed. These cochlear implant systems bypass the defective or missing hair cells located in the cochlea by presenting electrical stimulation directly to the ganglion cells in the cochlea. This electrical stimulation is supplied by an electrode array which is implanted in the cochlea. The ganglion cells then generate nerve impulses which are transmitted through the auditory nerve to the brain. This leads to the perception of sound in the brain and provides at least partial restoration of hearing function.

A cochlear prosthesis may typically comprise both an external unit that receives and processes ambient sound waves and an implant that receives data from the external unit and uses that data to directly stimulate the auditory nerve. Because the internal unit is surgically implanted, failure of the internal unit requires a surgical procedure to replace the damaged component. Failure of the internal unit may result from a variety of causes, such as damage from an impact.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

As mentioned above, a cochlear implant may be used to partially restore hearing in a patient by directly stimulating nerve cells. One component of the cochlear implant is an internal unit which is typically implanted underneath the skin above the ear. The internal unit receives signals from an exterior unit and transfers those signals into electrical impulses. These electrical impulses travel along wires which run from the internal unit to electrodes which directly stimulate the cochlea.

To prevent bodily fluids from damaging electronic components which may be present within the device, the circuitry included with the internal unit is often enclosed within a hermetically sealed case. An electrical feedthrough may be used to transfer signals from the circuitry inside the hermetic case to the exterior of the case and vice versa. This electrical feedthrough maintains the integrity of the hermetic seal, while allowing electrical signals to pass through.

To increase comfort and ease of implantation, as well as minimize surgical trauma, it is desirable that the cochlear implant be as small as possible. Depending on the design, reducing the size of the implant may also reduce the risk of damage to the implant from blows or impacts. However, reducing the size of the implant has the associated challenge of shrinking the size of the hermetic feedthroughs. Each hermetic feedthrough design has manufacturing and material limitations on how much they can be scaled down, i.e., there are limitations imposed by the fabrication method, structure, leak path, etc. of the feedthrough.

The present specification relates to an electrical feedthrough disposed within a metallic plate which forms a perimeter wall of a hermetically sealed case. According to one illustrative embodiment, the case may be generally cylindrical in shape having a large diameter to height ratio. The case may be hollow in the center so as to allow electrical circuitry to be placed within. The outer radial wall of the feedthrough material may be connected to the interior of a hole in the metallic material through a brazing or other joining process.

According to one illustrative embodiment, a small diameter electrical feedthrough is formed using a co-fired ceramic, either high temperature or low temperature. However, the ceramic feedthrough is not used as a hybrid circuit, but is used in combination with a separate hybrid circuit which is electrically connected to the feedthrough. This unique architecture allows the feedthrough to be as small as allowed by fabrication limits because it is not directly integrated with electrical components. This feedthrough architecture has several advantages that are difficult, if not impossible, to obtain with other feedthroughs. For example, the height and pitch can be reduced relative to pin-based feedthroughs; the mechanical reliability is increased relative to large co-fired feedthroughs; the smaller feedthrough can be located in different portions of a hermetic case; changes to the hybrid circuit do not mechanically affect the feedthrough; and the routing of the feedthrough can be optimized to maximize hermeticity and reliability.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1:
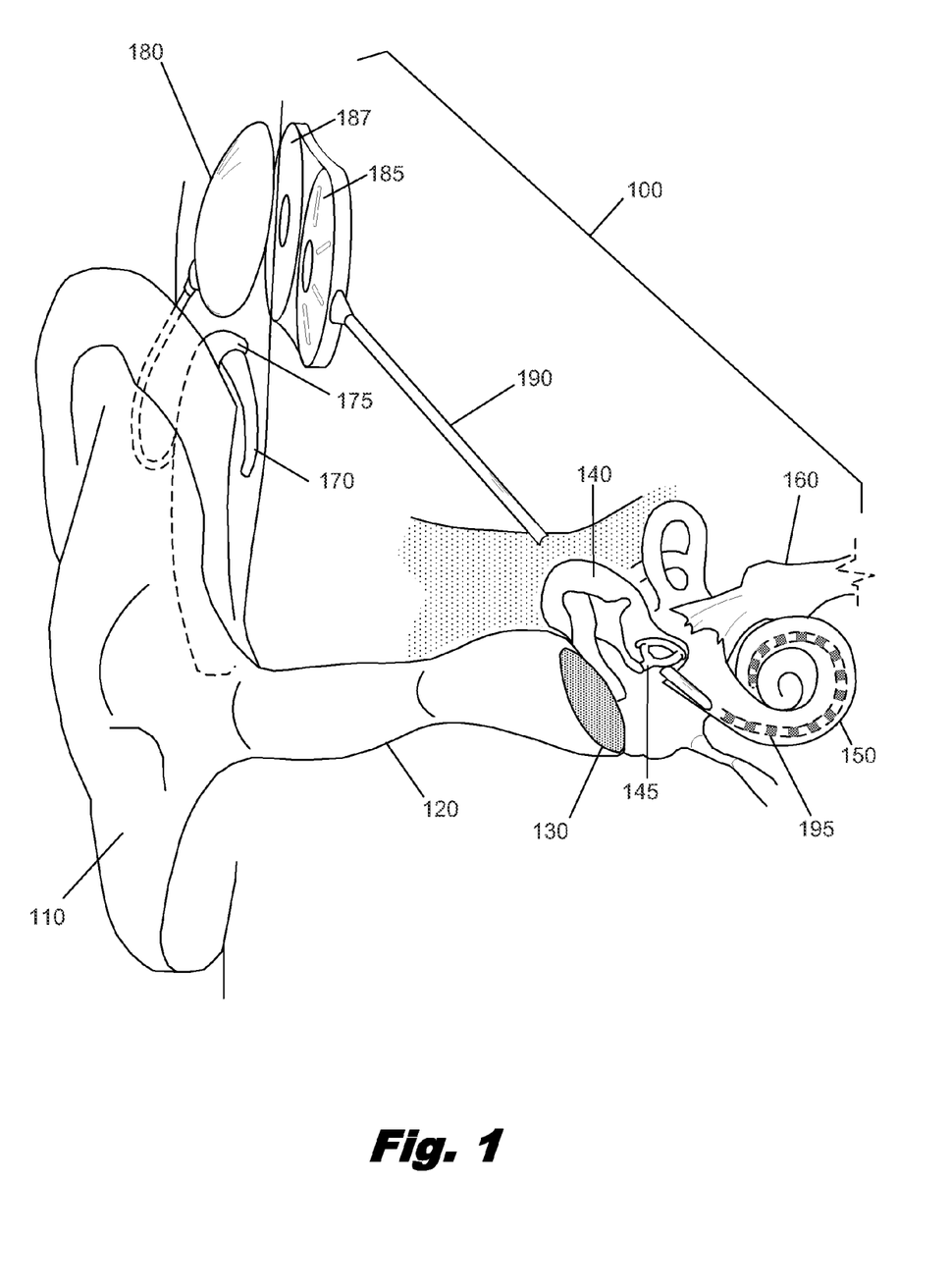
FIG. 1 is a diagram showing an illustrative cochlear implant system, according to one embodiment of principles described herein.

Referring now to the figures, FIG. 1 is a diagram showing one illustrative embodiment of a cochlear implant (100) surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third of the ossicles, or stirrup, (145) contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. As also noted above, in many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (100) does not amplify sound, but works by directly stimulating the auditory nerve (160) with electrical impulses. Consequently, providing a cochlear prosthesis typically involves the implantation of electrodes into the cochlea. The cochlear prosthesis operates by direct electrical stimulation of the auditory nerve cells, bypassing the defective cochlear hair cells that normally traduce acoustic energy into electrical energy.

External components of the cochlear implant include a microphone (170), speech processor (175), and transmitter (180). The microphone (170) picks up sound from the environment and converts it into electrical impulses. The speech processor (175) selectively filters and manipulates the electrical impulses and sends the processed electrical signals through a cable to the transmitter (180). The transmitter (180) receives the processed electrical signals from the processor (175) and transmits them to the cochlear implant (100) by electromagnetic induction and/or by using radio frequencies.

The cochlear implant (100) may include an antenna (87) and an internal processor (185). The antenna (187) and internal processor (185) are secured beneath the user's skin, typically above and behind the external ear (110). The internal processor (185) includes electronic circuitry housed in a hermetically sealed enclosure. This electronic circuitry is connected to via a hermetically sealed feedthrough to the antenna (187). The antenna (187) receives power and signals from the transmitter (180) via electromagnetic induction and/or radio frequency signals. The internal processor (185) processes the received signals and sends modified signals through a hermetic feedthrough to cochlear lead (190) and electrodes (195). The electrodes (195) are inserted into the cochlea (150) and provide electrical stimulation to the auditory nerve (160).

The implant works by using the tonotopic organization of the cochlea. The cochlea is arranged tonotopically, also referred to as "frequency-to-place" mapping. The tonotopic structure of the cochlea enables human beings to hear a broad range of acoustic frequencies. The nerve cells sense progressively lower frequencies from the basal end of the cochlea to the apex. For normal hearing, the brain is presented with the electrical signals from the different regions of the cochlea and, because of the tonotopic configuration of the cochlea, is able to discern the acoustic frequencies being heard. A cochlear implant simulates with its electrode contacts along the length of the cochlea to mimic this process.

Figure 2:
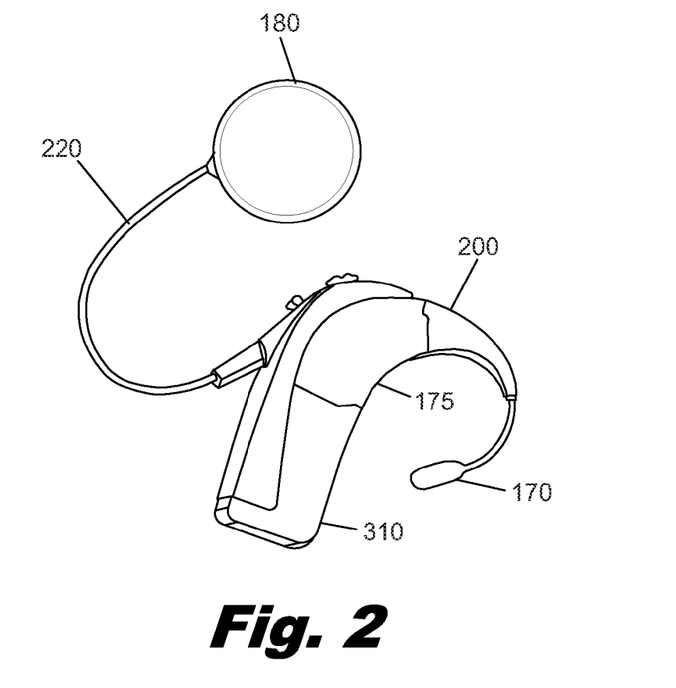
FIG. 2 is a diagram showing the external components of an illustrative cochlear implant system, according to one embodiment of principles described herein.

FIG. 2 shows one illustrative embodiment of the external components of the cochlear implant. The microphone (170) is attached to the ear hook (200). The ear hook (200) secures the external components behind the outer ear. The microphone (170) senses environmental sounds and converts those sounds into electrical impulses. The processor (175) filters and manipulates the electrical impulses it receives from the microphone (170) and transmits processed electrical sound signals along the external cable (220) to the transmitter (180). The processor (175), microphone (170) and transmitter (180) are powered by a battery (310).

Figure 3:
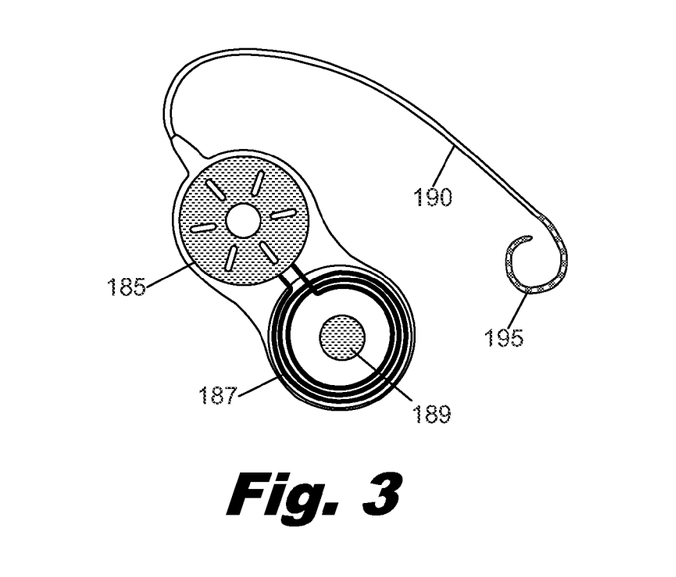
FIG. 3 is a diagram showing implanted components of an illustrative cochlear implant system, according to one embodiment of principles described herein.

FIG. 3 shows one illustrative embodiment of the internal components of the cochlear implant device. As described above, the antenna (187) is connected to the internal processor (185). According to one embodiment, the antenna (187) is a coned wire or wires that are encapsulated by a silicone overmold. A cavity within the center portion of the antenna (187) is adapted to receive a magnet (189). The transmitter (180) is held in place over the antenna (187) by magnetic interaction between components within the transmitter (180) and the implanted antenna magnet (189). The internal processor (185) is electrically connected to antenna (187) and receives signals and power via the antenna (187). The internal processor (185) is connected to the cochlear lead (190) which terminates in a flexible end that contains the electrodes (195). The electrodes (195) consist of a plurality of individual electrodes contacts made from platinum or a similar inert conductive material. These electrodes and associated wires are supported and connected by a flexible and durable biocompatible material, typically silicone rubber.

Figure 4A:
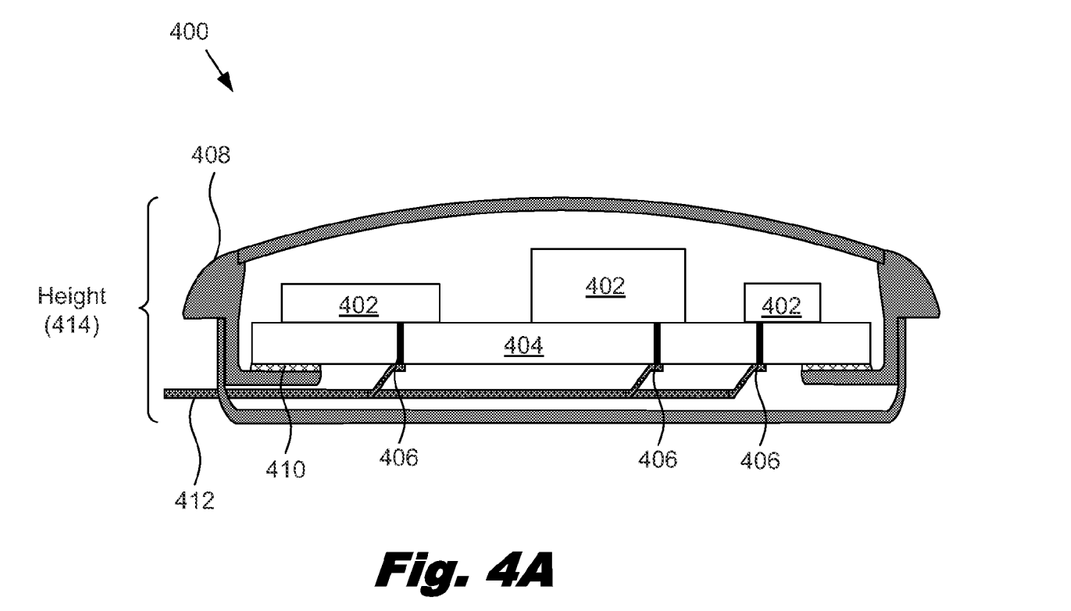
FIG. 4A is a diagram showing an illustrative hermetically sealed device with a large diameter electrical feedthrough which also serves as a hybrid circuit board, according to one embodiment of principles described herein.
Figure 4B:
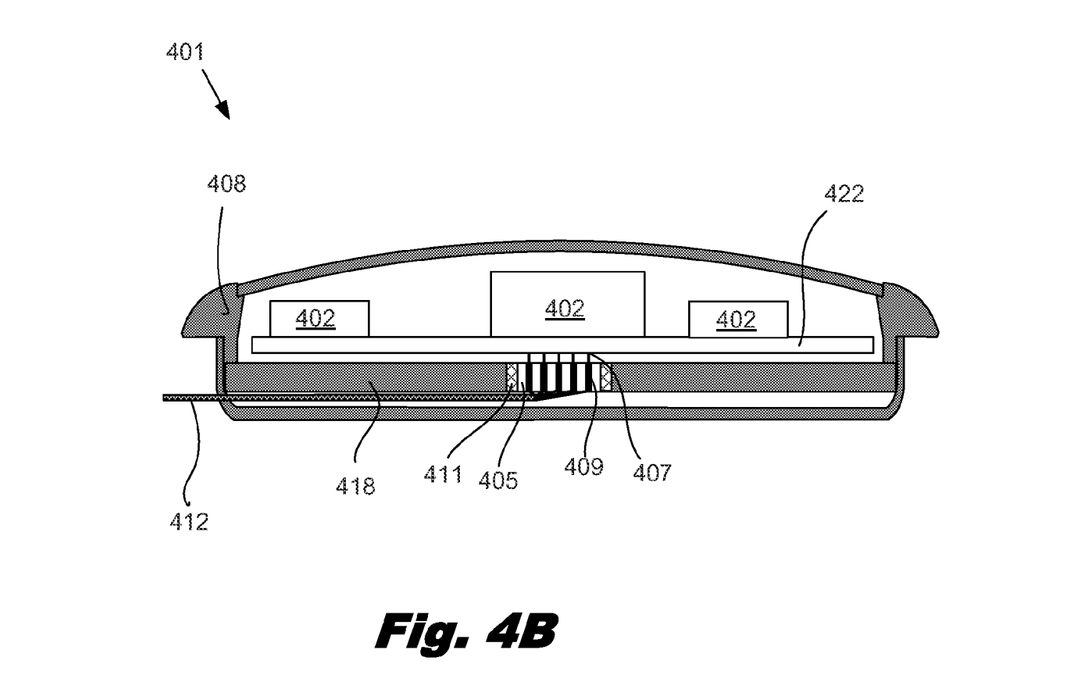
FIG. 4B is a diagram showing an illustrative hermetically sealed device with a small diameter electrical feedthrough, according to one embodiment of principles described herein.

FIGS. 4A and 4B show two alternative embodiments of ceramic feedthroughs (404, 405) which may be used in a cochlear implant (100). FIG. 4A illustrates a more conventional large diameter ceramic feedthrough (404) which also serves as hybrid circuit. FIG. 4B is a diagram of an illustrative small diameter ceramic feedthrough (405) which is separate from an interior hybrid circuit (422). Throughout the specification, various comparisons between the smaller modularized feedthrough (405) of FIG. 4B and the large diameter feedthrough (404) of FIG. 4A are made. As discussed below, the smaller modularized feedthrough (405) of FIG. 4B can be more robust, less expensive, and more versatile than the larger diameter feedthrough (404) of FIG. 4A.

FIG. 4A is a diagram showing one illustrative arrangement for a hermetically sealed portion (400) of the cochlear implant (100) containing the internal processor (185), which incorporates a large diameter hermetic feedthrough (404). The hermetically sealed portion (400) may include an outer case (408), the feedthrough (404), and internal electrical components (402)

The outer case (408) of the hermetically sealed portion (400) may be made of metallic material or other suitable material. According to one illustrative embodiment, the outer casing is made up of a multiple pieces. These pieces may be connected through a variety of methods including, but not limited to, brazing, welding or gluing. One of such pieces may be an electrical feedthrough (404). The feedthrough (404) contains a number electrical vies (406).

According to one illustrative embodiment, the feedthrough (404) may be made of a ceramic material. The feedthrough (404) is connected to the outer case (408) through a braze joint (410) which is sandwiched between the ceramic feedthrough (404) and the case (408). To maintain the integrity of the feedthrough (404) and improve its impact resistance, the feedthrough is relatively thick. Additionally, some amount of flexure in the components surrounding the feedthrough may be desirable. This flexure accommodates any thermally induced differences in dimension between the ceramic feedthrough (404) and the other components. The sandwich style braze joint (410), feedthrough thickness, and flexure design may increase the overall height (414) of the hermetically sealed case.

FIG. 4B is a diagram showing an illustrative hermetically sealed device (401) which includes a reduced diameter ceramic feedthrough (405). According to certain embodiments, a metallic plate (418) may form the bottom of the hermetic enclosure. For example, the metallic plate (418) may be formed from titanium or a titanium alloy. An aperture may be formed within the metallic plate (418). The aperture may have a variety of shapes, including circular, elliptical, or other suitable shapes. The reduced diameter ceramic feedthrough (405) may then be placed within that aperture. The feedthrough (405) may be hermetically joined to the metallic plate (418) using a variety of techniques to form a joint (411). For example, the radial wall of the feedthrough (405) may be brazed to the interior region of the aperture formed in the metallic plate (418). The braze material may be any suitable bio-compatible metal or alloy which is typically used in brazing processes. Although a compression braze is illustrated in FIG. 4B, a variety of other connection geometries could be used. By way of example and not limitation, a flange may be incorporated into the design. The flange may have a number of benefits, including increasing the diffusion path through the joint, increasing the bonding area, and holding the ceramic feedthrough in place during the joining operation. In an alternative embodiment, the feedthrough may be first joined to a metal flange using an appropriate joining technique. The metal flange may then be laser welded to the metallic plate.

The dimension of the feedthrough (405) may be much smaller than the diameter of the metallic plate (418) in which the feedthrough is placed. In some embodiments, the electrical paths which pass through the feedthrough (405) may be as small as allowed by fabrication limits of the manufacturing process or electrical constraints of the overall electronic design (such as resistance, current, capacitance, etc.). This results in much smaller feedthroughs (405) which can be located in different portions of a hermetic case.

A wiring harness (412) includes a number of wires which are attached to the vias (409). According to one illustrative embodiment, the wires are connected to the vias (409) using a welding process, such as laser welding or electrical resistance welding. A variety of other connection techniques may be used, including wire bonding, tape automated bonding, and soldering.

A hybrid circuit (422) may be used in conjunction with the smaller diameter feedthrough (405) rather than directly attaching electronic components to a larger diameter feedthrough (404) as illustrated in FIG. 4A. As used in the specification and appended claims, the term "hybrid circuit" refers to a miniaturized circuit which contains a multilayer circuit board and electrical components which are mounted to the multilayer circuit board. For example, the hybrid circuit (422) may be a ceramic hybrid circuit, an organic hybrid, or a co-fired ceramic. According to one illustrative embodiment, this multilayer circuit board may be a low temperature co-fired ceramic circuit board which incorporates a number of passive electronic devices. The hybrid circuit (422) may be encapsulated in epoxy. A hybrid circuit differs from an integrated circuit in that it allows for circuitry containing certain types of electronic components, such as large value capacitors and inductors, to be directly incorporated. The hybrid circuit (422) may be configured so that traces run from the attached electrical components (402) to a location that matches the electrical vias of the feedthrough material.

On the interior side of the electrical feedthrough (405), connections (407) may be made between the hybrid circuit (422) and the feedthrough (405). According to one illustrative embodiment, the hybrid circuit (422) is attached to the underlying electrical feedthrough (405) using a blind attachment technique. Blind attachment refers to situations where only one side of a workpiece is accessible for component assembly and making electrical connections. In this case, the hybrid circuit (422) may entirely cover the electrical feedthrough (405), rendering it not visible during the attachment process. The blind attachment may be done using a variety of methods including, but not limited to anisotropic-conductive film, anisotropic-conductive paste, conductive epoxy, conductive silicone, solder, ball-grid array, and other compatible approaches.

The reduced diameter feedthrough (405) may have a number of advantages over the configuration shown in FIG. 4A. The braze system may be chosen so that the ceramic has a residual compressive stress to inhibit crack propagation. The ceramic has a reduced diameter and less volume decreasing the probability of the ceramic containing critical defects that can lead to failures.

Figure 4C:
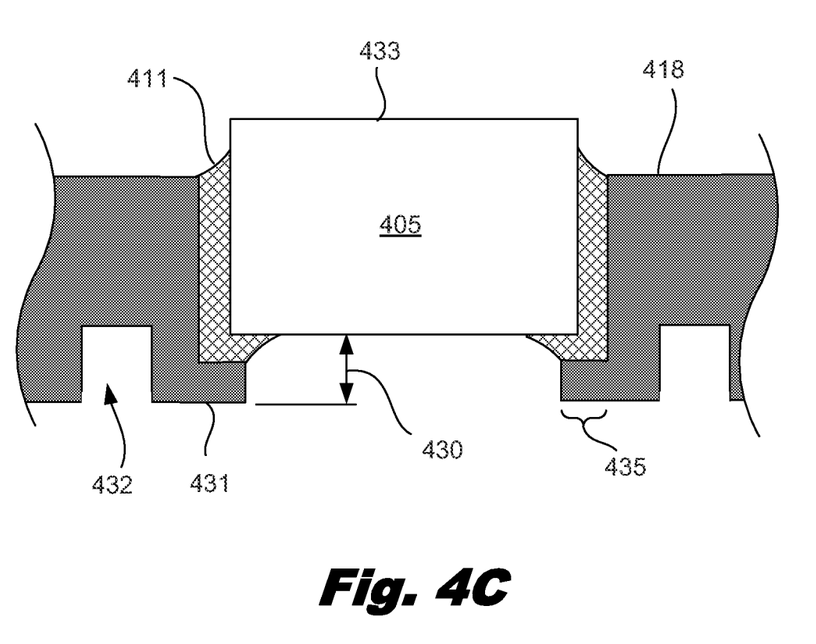
FIG. 4C is a diagram showing an illustrative small diameter electrical feedthrough which is joined to a metallic plate, according to one embodiment of principles described herein.

FIG. 4C is a cross sectional diagram of a reduced diameter ceramic feedthrough (405) joined to a metallic plate (418) by a joint (411). According to one illustrative embodiment, the loads transmitted from the metallic plate (418) to the feedthrough (405) could be further reduced in a number of ways. For example, the ceramic feedthrough (405) could be slightly recessed into the metallic plate (418). This offset (430) from the exterior surface (431) of the metallic plate (418) could prevent the direct application of forces to the ceramic feedthrough (405) during an impact event. This may also result in the extension of the inner surface (433) of the ceramic feedthrough into the interior of the case. This could simplify the blind bonding of the hybrid circuit to the ceramic feedthrough (405) and reduce the likelihood of shorting to the metallic plate (418).

In this embodiment, a flange (435) is included in the aperture formed in the metallic plate (418). As discussed above, the flange (435) may have a number of benefits, including increasing the diffusion path through the joint, increasing the bonding area, and holding the ceramic feedthrough (405) in place during the joining operation.

Additionally or alternatively, a groove, slot or other thickness-reducing feature (432) may reduce the stresses transferred from the metallic plate (418) to the ceramic feedthrough (405). These features (432) may allow for small amounts of flexure of the metal surrounding the feedthrough (405). This deformation may accommodate an increased level of impact or thermal related stress without causing damage to the ceramic feedthrough (405). The thickness-reducing features (432) may be formed in the one or both sides of the metallic plate (418).

As shown in FIG. 4B, the small diameter electrical feedthrough (405) may be formed using a co-fired ceramic and does not have any electronic components directly mounted to it. Instead, electrical connections are made between the electrical feedthrough and the hybrid circuit, which may also be formed from co-fired ceramic. This modularization is counterintuitive to those of so skill in the art for at least the following reasons. It is well known in the art that co-fired ceramic feedthroughs are well adapted to simultaneously serve as electrical feedthroughs, impermeable walls in hermetic enclosures, and attachment surfaces for electronics. Consequently, using two separate co-fired ceramic pieces or a co-fired feedthrough and a separate hybrid circuit, one for an electrical feedthrough and another as a hybrid circuit runs counter to several accepted design rules. For example, one of ordinary skill in the art would view a design which includes two co-fired ceramic pieces as unnecessarily increasing the cost, complexity, and size of an implant.

However, use of two separate components provides a number of benefits which are not provided by the conventional co-fired feedthrough and would not be apparent to one of skill in the art. First, by separating the co-fired feedthrough from electronics, the co-fired feedthrough no longer has to provide surface area on which to mount the electronics. This allows the size of the co-fired feedthrough to be drastically reduced. In some embodiments, the co-fired So ceramic feedthrough may use minimum sized features. For example, if the minimum feature size of a particular manufacturing process is 5 mils, the individual vias and spacing between the vias could be on the order of 5 mils. This surprising reduction in size can significantly improve the reliability of the implant.

Second, the miniaturization of the feedthrough can allow the feedthrough to be located to in portions of the implant case where feedthroughs have not been previously viable. In cochlear implants, conventional large diameter feedthroughs are so large that they can only be located in the top and bottom of the cylindrical cases. These feedthroughs are located on the bottom of the case to provide additional protection to the wiring harnesses and electrical connections between the wiring harness and the electrical feedthrough. However, as discussed below, the miniaturization of the feedthrough allows the feedthrough to be located in the sidewall of the cylindrical case. This can reduce the overall height of the implant because the wiring is no longer underneath the implant. It can also increase the ruggedness of the implant because the implant can have a continuous metal bottom. Further, a side wall mounted feedthrough may reduce the overall wiring length and provide a convenient location for a connectorized harness.

The reduced diameter feedthrough (405) may be the reduction of the overall height of the implanted device compared to pin-based approaches. For most pin-based approaches the height of the implant will be driven by the need to include a braze length that provides a suitable leak path and enough space for the pins to extend sufficiently beyond the braze joint for bonding on both sides of the feedthrough.

Modularization of the electrical feedthrough can provide additional flexibility and reduced expense in changing the design of the hybrid circuit. In the illustrative embodiment of FIG. 4A, the larger diameter feedthrough (404) is both the feedthrough and the circuit board on which the electrical components are mounted. For this configuration, almost any change in electrical design will result in a change to the electrical feedthrough (404). This can be undesirable because changes to the electrical feedthrough (404) can result in the need for retesting the device to ensure that the change has not reduced the impact resistance of the implanted device, introduced stress/thermal expansion issues or caused other issues. By separating/modularizing the feedthrough (405) and the hybrid circuit (422), the hybrid circuit (422) can be changed without affecting the feedthrough design. This keeps the structural components of the implanted device and the interface between the device and human tissue the same. Consequently, a change to the electronic circuit will not affect mechanical reliability.

Figure 5:
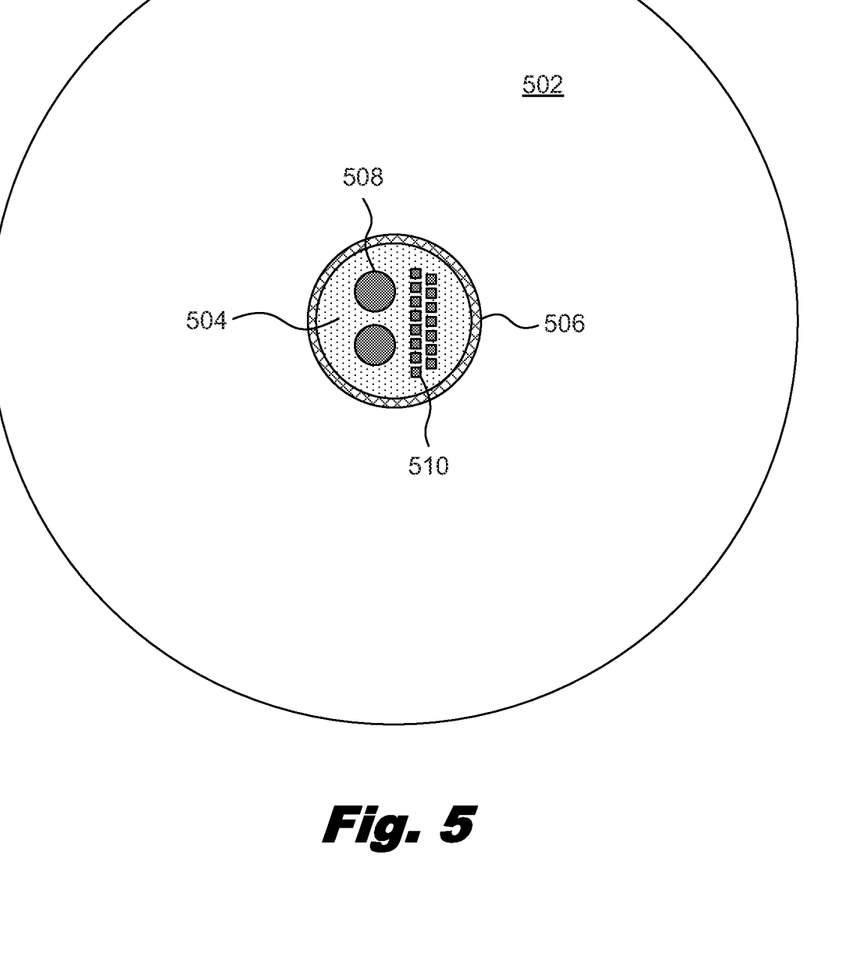
FIG. 5 is a top view of an illustrative metallic plate having an electrical feedthrough disposed within, according to one embodiment of principles described herein.

FIG. 5 is a top view of an illustrative metallic plate (502) with an electrical feedthrough (504) disposed within. As mentioned above, the perimeter of the feedthrough (504) may be connected to the interior of the aperture in the metallic plate (502) using a braze joint (506) or other suitable methods.

A number of brazing techniques can be used to form a hermetically sealed braze joint (506) between the metallic plate (502) and the ceramic feedthrough (504). For example, the ceramic feedthrough (504) could be metalized on its perimeter to provide a surface to which the braze material adheres. The metallization of the ceramic surface may be accomplished in a number of ways. By way of example and not limitation, conductive portions of ceramics can be coated by screen printing using platinum, titanium, nickel, gold, or other suitable metals or metal combinations. The materials used in implanted devices must be carefully selected for long term reliability and chemical stability. Particularly, the materials must not have significant adverse effects on the patient's health. For example, metal combinations with a large percentage of copper are typically avoided because copper has a tendency to corrode when implanted, thereby releasing copper oxides and other copper derivatives into the surrounding tissues.

In an alternative embodiment, a metal hydride or active braze could be used to join the ceramic feedthrough (405) and the feedthrough case (408). The metal hydride and active brazes possess the ability to wet ceramic surfaces that have not been previously metalized. For example, a hydride, usually of titanium or zirconium, is reduced and brazed simultaneously in a controlled atmosphere. In one embodiment, following the metal hydride application, a platinum, gold, other suitable metals, or other eutectic braze alloys can then used in the brazing process. For hermetic feedthroughs which are not used in implantable devices, the range of available materials is even greater and may include metals or metal alloys such include copper and nickel.

An active metal typically uses a layered structure of two metals that have a eutectic point in their phase diagram. The braze perform melts at the eutectic composition and the melt joins the ceramic to the metal case. This process can eliminate the need to metalize the ceramic prior to brazing. By way of example and not limitation, these active elements may include titanium, zirconium, hafnium, vanadium, and aluminum or combinations thereof. According to one illustrative embodiment, the active braze material may be approximately 50% titanium and 50% nickel.

According to one embodiment, the braze joint may incorporate ceramic particulates. These ceramic particulates can increase the strength of the braze material, decrease its permeability, and reduce its coefficient of thermal expansion to more closely match the ceramic material. In one embodiment, the inclusion of as little of 5% (by volume) of ceramic particulates increases the strength of the reinforced active metal alloy over un-reinforced active metal alloy by approximately 30%. By including ceramic particulates in the braze joint, the joint is less likely to fail when subjected to temperature extremes or other forces.

For example, subsequent manufacturing processes, such as welding and soldering, may heat the ceramic and or titanium components of the case. The inclusion of ceramic particulates provides a braze material with an intermediate coefficient of thermal expansion that is greater than the ceramic but lower than the adjoining metal. The braze joint then acts as a buffer which reduces the thermal stress at any one surface and makes the joint less likely to fail at either the metal or ceramic interface.

According to one illustrative embodiment, a compression braze joint may be used to secure the ceramic feedthrough (504) in a titanium plate (502). The compression braze joint (506) may be formed by first heating the ceramic feedthrough (504) and the titanium plate (502) to a temperature which above the melting point of the braze material. Typically the braze material is drawn by capillary action into the joint. The assembly is then cooled. At some point in the cooling process, the braze material solidifies. As the assembly continues to cool, the titanium plate contracts slightly more than the ceramic feedthrough. This compresses both the braze joint (506) and the ceramic feedthrough. It is intended that the residual compression stress inhibit crack propagation by imposing a closure stress on any cracks or flaws, which typically grow under a mode|driving force, i.e., tensile opening. However, it is understood that at small size scales and with multiple interfaces there may be mixed-mode loading conditions for cracks or defects in the feedthrough that can affect the driving force for crack propagation and the performance of the feedthrough.

Figure 6:
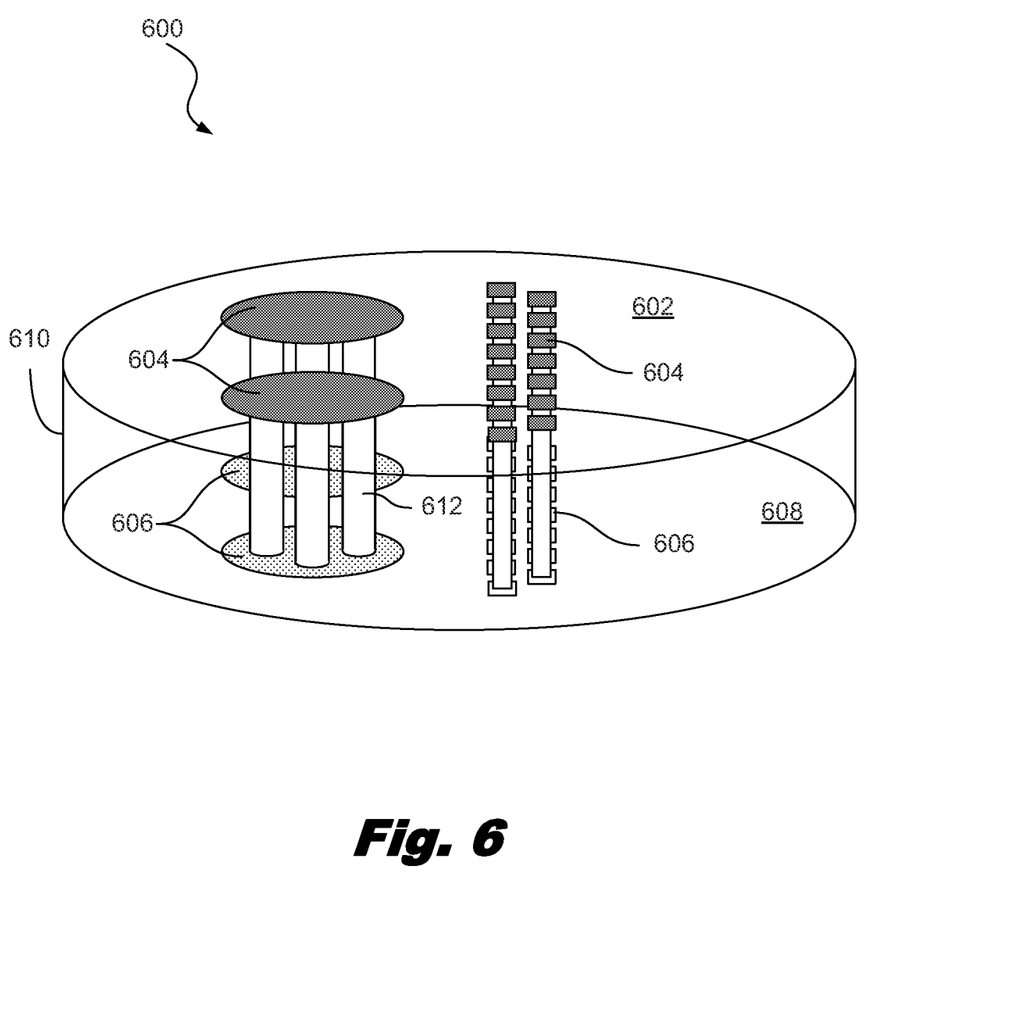
FIG. 6 is a wire frame view of an illustrative electrical feedthrough, according to one embodiment of principles described herein.

The electrical vias (508, 510) may have a variety of shapes and geometries. According to one illustrative embodiment, the vies (510) may have a cross section which is on the order of 5 to 10 mils in diameter. Other larger electrical paths (508) may be formed where a lower resistance is particularly desirable or where higher current flow occurs. The spacing between the vias may be approximately 5-10 mils. For 5 mil vies with 5 mil spacing, the center-to-center pitch between vies is 10 mils. This results in linear via density of 100 vias per inch and a via density of approximately 10,000 vias per square inch. The ratio of the device diameter to the feedthrough diameter in this example is 15 to 1. According to one illustrative embodiment, the device diameter to the feedthrough diameter is greater then 5 to 1. These small diameter feedthroughs can significantly increase the robustness of the implant device FIG. 6 is a wire frame view of an illustrative feedthrough (600) which includes a number of electrical vias (612). According to certain illustrative embodiments, the vias (612) pass through feedthrough (610) and may include a top metalized connection pad (604) on a top side (602) and a bottom metalized connection pad (606) on a bottom side (608) of the feedthrough (610).

According to certain illustrative embodiments, a number of vies (612) may be grouped together and share the same connection pads (604, 606) on either or both ends. Grouping them on both ends will reduce the electrical resistance measured between top metallic connection pad (604) and the bottom metallic connection pad (606) because electrical current can flow through all of the connected vias. This lower resistance may be beneficial for some signals. For example, the signals coming in from the antenna may be more prone to unacceptable signal degradation. Thus, it may be desirable to have the signals from the antenna travel through a via within the feedthrough where electrical resistance is minimized. Other electrical connections may have smaller connection pads and use only one via for conduction of electricity through the feedthrough. These individual electrical paths may be used for conducting electrical signals which have less current or are less sensitive to high connection resistances. For example, the individual vias may be used to pass electrical signals out of the processor and into the cochlear lead.

In some alternative embodiments, the vias (612) within the feedthrough (610) may have more complex routing. For example, a via may connect to two or more pads, branch, and/or interconnect with other vias. In some embodiments, vias may attach to ground planes or form shielding around or between other vias.

In certain embodiments, the metallic connection pad (604) on the interior side (602) may comprise a different material than the metallic connection pad (606) on the exterior side (608) of the feedthrough (610). For example, it may be beneficial to use platinum on the exterior side (608), as that side will be in contact with human tissue. It may be advantageous to use a material such as gold for the metallic plating (604) on the interior side (602), as that side will be in contact with the internal circuitry.

A variety of structures could be used to create a feedthrough (610) with vias (612). For example, a feedthrough may be formed from a monolithic slab of conductive material by fabricating electrically isolated pins out of the monolithic slab. This technique is described in U.S. App. No. 61/286,700, entitled "Hermetic Electrical Feedthrough" to Kurt J. Koester et al. which is incorporated herein by reference in its entirety. Other techniques may also be used, including the techniques described below.

Figure 7:
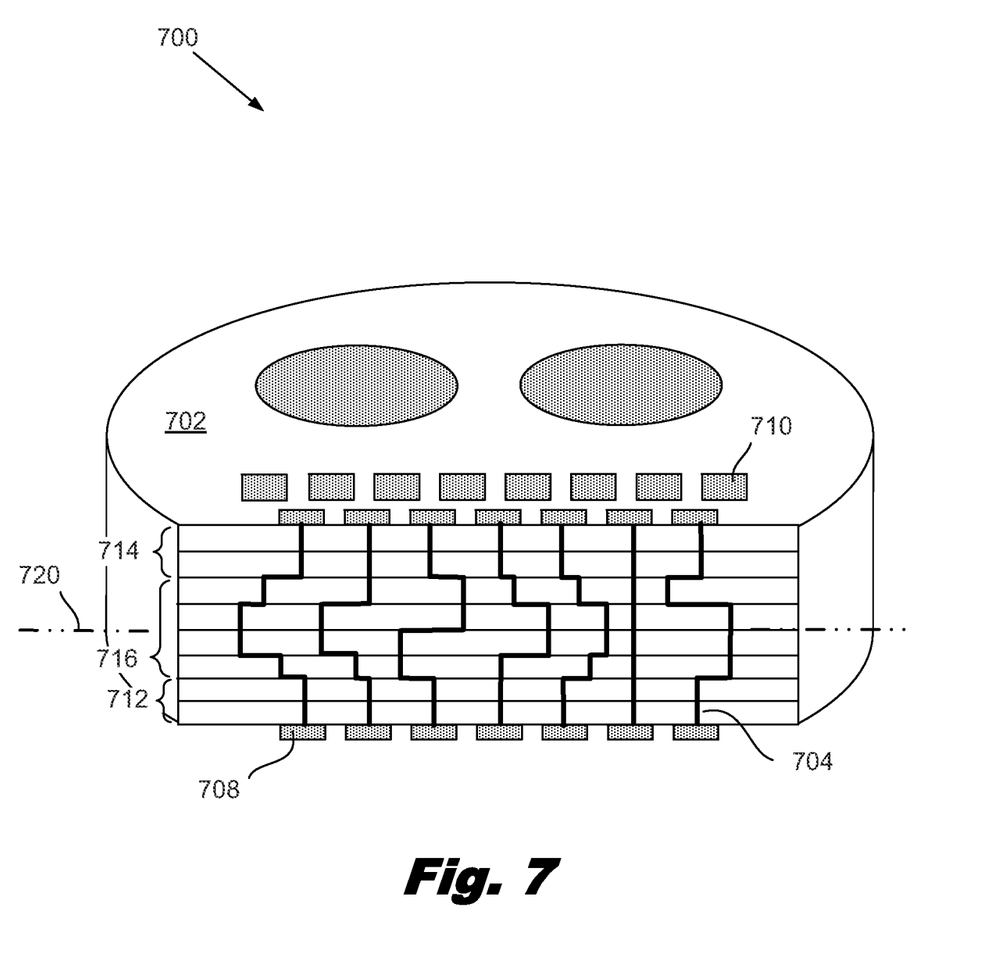
FIG. 7 is a cross sectional diagram showing the path of electrical vias through a feedthrough, according to one embodiment of principles described herein.

FIG. 7 is a diagram showing an illustrative cross-sectional view of electrical vias jogged through a feedthrough (700). According to certain embodiments, the feedthrough (700) may be made of a multilayer co-fired ceramic material. Such a material may be formed having electrical traces formed between each layer. Electrical vias (704) may then run between the traces of adjacent layers (706). The electrical vias ultimately form a serpentine route between a metallic pad (708) on one side of the feedthrough (700) to a metallic pad (710) on the other side of the feedthrough (700).

The serpentine shape of the electrical vias (704) can provide several benefits. First, the serpentine path of the electrical vias (704) can be used to route the electrical connection to a different location on the inner surface of the feedthrough (700). Second, discontinuities in the feedthrough (700), such as interfaces between the vies and the surrounding matrix can provide paths along which vapor or liquid tends to travel. The serpentine path may create a longer diffusion path for any vapor or liquid through the feedthrough (700) and decrease the overall permeability of the ceramic feedthrough (700).

However, it is believed that the serpentine conduction paths may increase or decrease the overall toughness of the ceramic feedthrough (700) depending on material properties, loading conditions, and other factors. The benefits and advantages of creating serpentine conduction paths through the ceramic feedthrough (700) can be evaluated for a given design and appropriately implemented. Consequently, for a given design, a feedthrough may or may not have serpentine conduction paths.

As discussed above, ceramics fail mechanically due to crack propagation. Therefore, a goal of the feedthrough assembly design is to minimize the driving force for crack propagation. Typically, this corresponds to minimizing the tensile stress. Depending on feedthrough assembly geometry, position within the body, and location and direction of applied force, during impact events, the exterior outer layers (712) or interior outer layers (714) of the feedthrough (700) may be subject to more tensile stress than the more central layers (716) that are closer to the neutral axis (720). The exact position of the neutral axis will depend on the layout of the materials and the loading conditions, but a reasonable estimate is that the neutral axis coincides with the midplane of the cross section. For example, when a force is applied to an edge of an implanted case (408) (see, for example, FIGS. 4A and 4B), the force may be transmitted to the edge of the ceramic feedthrough such that the interior outer layers (714) of the ceramic are in tension and the exterior outer layers (712) of the ceramic are in compression. Forces applied to other regions of the implant device may have a different effect, for example, causing compression in the interior layers and tension in the exterior outer layers. Sudden changes in via direction can result in stress concentrations. One technique for increasing the strength of the ceramic feedthrough is to design the vias such that they pass straight through two or more outer layers (712, 714), and then jog in the central layers (716) where lower stress levels mitigate the influence of the sharp discontinuities in via directions. Carefully constructing outer layers with reduced levels of defects and via jogs can result in a surprising increase robustness of the ceramic feedthrough (700).

The geometry of the electrical vies can be selected to provide the desired balance between toughness and impermeability of the feedthrough. For example, if toughness is the primary design factor, the vias can be straight. If impermeability is the primary design factor, the vies may follow long convoluted paths through the ceramic feedthrough. Typically, a balance between toughness and impermeability, as well as other factors such as size, cost, and manufacturability is desired. Consequently, the geometry of the vias may be selected to provide a balance between toughness, impermeability, and other factors. As discussed above, this balance may include forming straight portions of the vies through the more highly stressed outer layers of the ceramic feedthrough and jogging the vies in the lower stressed interior layers to increase the impermeability of the feedthrough. As shown in FIG. 7, the vies may have a variety of configurations which may vary from via to via. According to one illustrative embodiment, the geometry of a particular via may be at least partially dependent on the location of the via within the feedthrough. For example, vies which are closer to an edge of the feedthrough may have a different geometry than vies which are in the center of the feedthrough.

According to one illustrative embodiment, the electrical vies (704) may be formed from two or more conductive metals. The composition of the electrical via (704) may change through the thickness of the feedthrough. For example, in the exterior layers a via may be formed from a more biocompatible material such as platinum or titanium. In interior layers, the via may be formed from a different material which has one or more characteristics which are mechanically or electrically superior to the more biocompatible material. The interior layers are protected from biological contact by the exterior layers. Consequently, there may be a wider range of materials which may be suitable for use. For example, portions of a via which pass through the interior layers may be formed from gold or a gold alloy. Gold may have superior electrical and bonding properties, but is not as inert as platinum.

Figure 8:
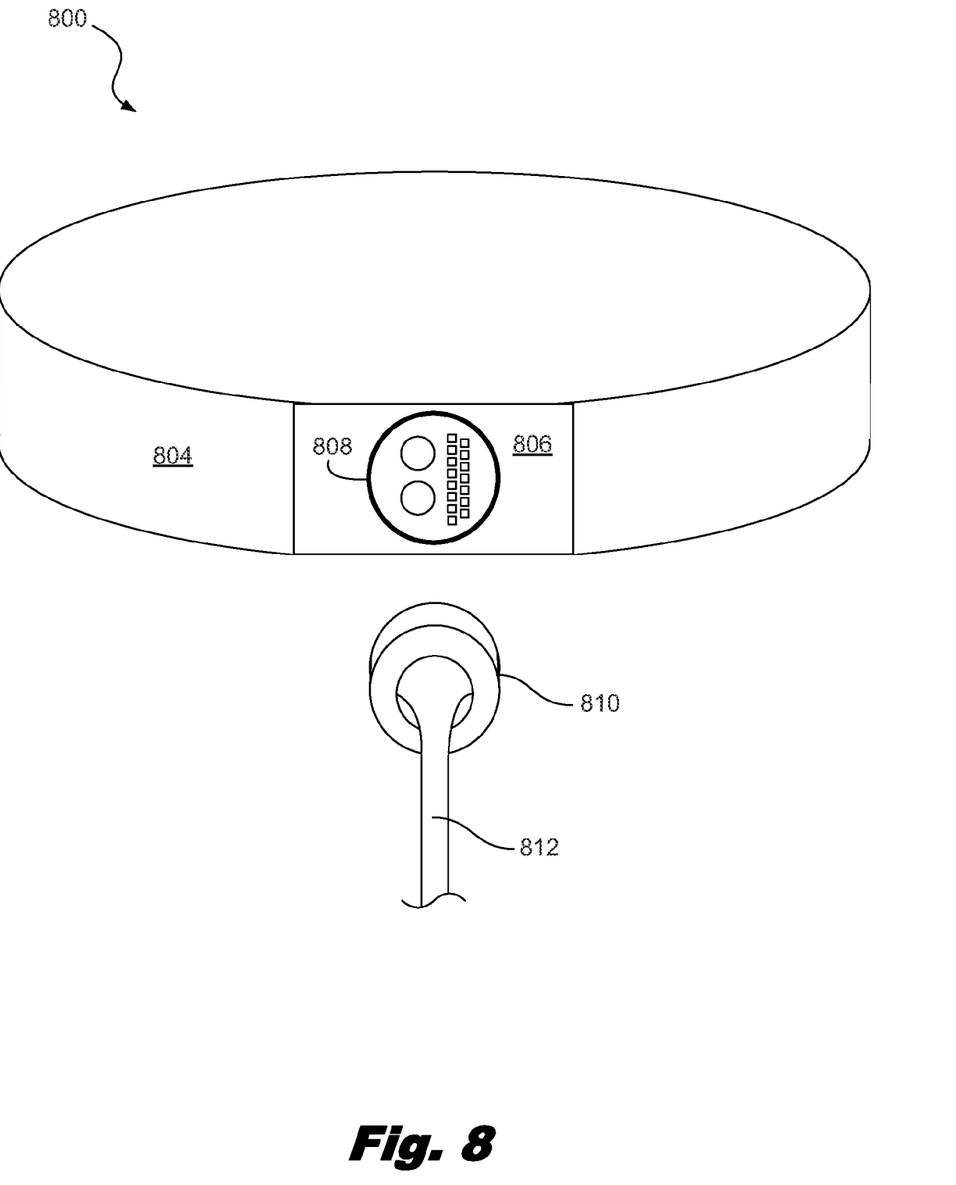
FIG. 8 is a diagram showing an illustrative hermetically sealed device having an electrical feedthrough on a radial wall, according to one embodiment of principles described herein.

FIG. 8 is a diagram showing an illustrative hermetically sealed device (800) having a small feedthrough (808) on a radial wall (804). The outer radial wall (804) of the elliptically shaped hermetically sealed device (800) may have a flat section (806) in which to place the feedthrough (808).

In certain embodiments, a connector (810) may be configured to connect the wires (812) which run to the electrodes and the antenna directly to the electrical vias in the feedthrough (808). The head of the connector (810) may be shaped to match the electrical vias in the feedthrough (808). The connector may be standardized so that new designs to the implant device may still be compatible with older electrode and antenna components or vice versa. In some embodiments, the connector and feedthrough may be configured such that the connector is detachable from and re-attachable to the feedthrough. This may advantageously allow hermetically sealed electronics to be replaced without removing the cochlear electrode array from the cochlea. The cochlear electrode array could simply be disconnected from the hermetically sealed electronics and reattached to a new or upgraded hermetically sealed electronic package.

Figure 9:
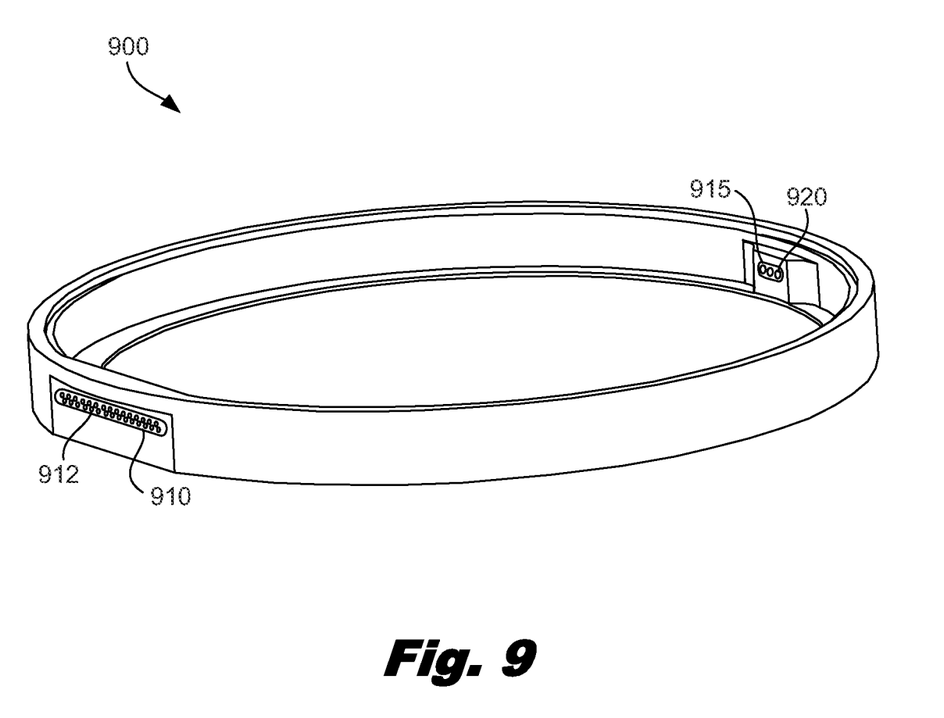
FIG. 9 is a diagram showing an illustrative housing component with electrical feedthroughs in a radial wall, according to one embodiment of principles described herein.

FIG. 9 is a diagram showing an illustrative housing component (900) with electrical feedthroughs (910, 915) in its radial wall. In this embodiment, the housing component (900) is a ring that forms the perimeter of a hermetically sealed device. Two feedthroughs (910, 915) are formed in opposite sides of the component (900). This is only one illustrative embodiment of a component which could incorporate feedthroughs. The feedthroughs (910, 915) could be incorporated in a variety of locations and in a variety of components which are used to form a hermetically sealed device.

The feedthroughs (910, 915) in this embodiment include linear arrays of vias (912, 920). This allows the feedthroughs (910, 915) to include a large number of vias while reducing the overall height of the feedthroughs (910, 915) and housing component (900). For example, the overall height of the feedthroughs (910, 915) may be on the order of 0.030-0.040 inches. The feedthroughs (910, 915) are then thin enough that the height of the electronics and circuit board will dominate the height of the implant.

As shown in FIG. 9, there may be various feedthroughs formed in different locations of the component (900). The locations and number of pins in each feedthrough can be adjusted to best suit a given design. In this illustrative embodiment, the smaller feedthrough (915) has three larger vias (920) which may be used to couple to the antenna (187) (FIG. 1) to communicate with and supply electrical power to the hermetically sealed portion (400) of the cochlear implant (100). On the opposite side of the component (900), the larger feedthrough (910) has a greater number of smaller vias (912) which can be used to conduct electrical signals to various implanted electrodes (195) (FIG. 1).

Figure 10:
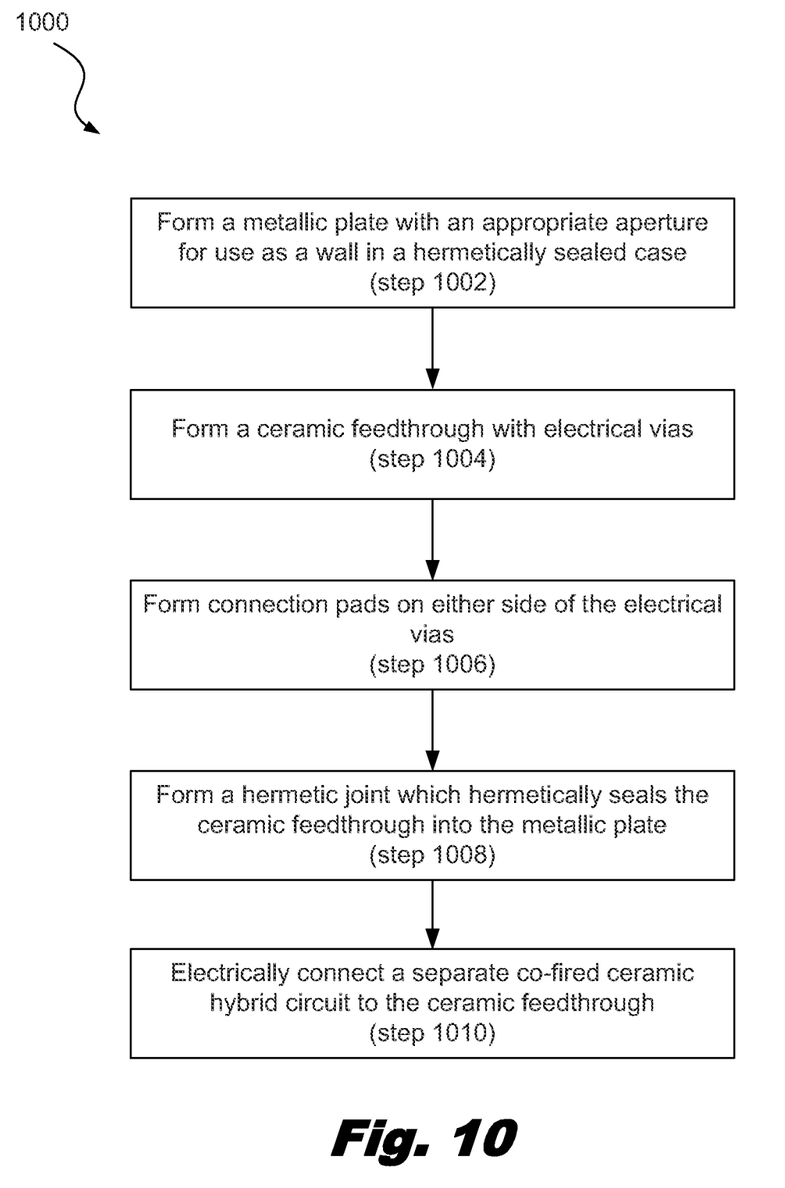
FIG. 10 is a flowchart showing an illustrative method for fabricating a feedthrough for a hermetically sealed device, according to one embodiment of principles described herein.

FIG. 10 is a flowchart showing an illustrative method (1000) for fabricating a feedthrough for a hermetically sealed device. According to one illustrative embodiment, the method (1000) may include forming (step 1002) a metallic plate with an appropriate aperture for use as a wall in a hermetically sealed device. For example, the aperture may be formed through a material removal process such as machining, laser machining, etching, electrical discharge machining, abrasive flow machining, electrochemical machining or other suitable process. Additionally or alternatively, the aperture may be formed in the metallic plate during a casting or sintering process. The metallic plate may be made from a variety of materials including titanium, platinum, gold, stainless steel and various alloys.

A ceramic feedthrough is then formed with a number of electrical vias (step 1004). As discussed above, the ceramic feedthrough may be formed in a variety of ways including using patterned green ceramic tape lay up and low temperature ceramic co-firing. The geometry of the vias can be selected to provide the desired balance between the toughness of the feedthrough and impermeability. For example, for a tougher and more impact resistant feedthrough, the vias may pass straight through two or more adjacent outer layers of the feedthrough. To increase the impermeability of the feedthrough, the vias may jog through the central layers of the feedthrough. Before firing, the ceramic feedthrough may be machined to ensure that the feedthrough has the proper shape and size to be brazed in the hole in the metallic plate. Connection pads are formed on either side of the electrical vias (step 1006). The connection pads may be formed in a variety of ways, including silk screening, lithographic, and other deposition techniques.

A hermetic joint is formed to seal the ceramic feedthrough into the metallic plate (step 1008). For example, a compression braze joint may be used to hermetically seal the ceramic feedthrough into the metallic plate. According to one illustrative embodiment, the ceramic feedthrough and metallic plate materials may be specifically selected such that they have a slight mismatch in CTE, with the CTE of the ceramic feedthrough being less than that of the braze materials and the metallic plate. The ceramic feedthrough and metallic plate are heated above a melting or softening point of a braze material. According to one illustrative embodiment, the braze material may be deposited in the joint prior to heating. For example, the braze material may be previously deposited on the ceramic feedthrough and/or metallic plate prior to heating. After the braze material has adhered to both the ceramic feedthrough and the metallic plate and substantially filled the joint volume, the temperature is reduced. As the temperature is reduced, the braze material solidifies and the metallic plate compresses the ceramic feedthrough and braze material. According to one illustrative embodiment, the ceramic feedthrough has a circular shape which distributes the stress more uniformly through the volume of the shape. However, the ceramic feedthrough may have any of a number of shapes, including oval, elliptical, rectangular, square, or other suitable shape. In most embodiments, sharp corners can be avoided to reduce the likelihood of stress concentrations and fractures.

The internal and external components can then be attached to the feedthrough. For example, an electrical connection could be made between a separate co-fired ceramic hybrid circuit and the feedthrough (step 1010). An external connection could be made between a wiring harness and the feedthrough. The wires could be connected in a variety of ways, including wire bonding and resistance welding techniques. In some embodiments, the external connection may be made to a connector.

In sum, a small diameter modularized feedthrough may provide a number of advantages including closer via spacing, increased mechanical reliability relative to large co--fired feedthroughs; the much smaller feedthrough can be located in different portions of a hermetic case; changes to the hybrid circuit do not mechanically affect the feedthrough; and the routing of the feedthrough can be optimized to maximize hermeticity and reliability.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A device comprising:
a hermetically sealed case with electronic circuitry housed within; in which one surface of the hermetically sealed case comprises:
a metallic plate;
a co-fired ceramic electrical feedthrough comprising a number of vias being hermetically joined to the metallic plate, wherein a ratio of a length of the metal plate to a length of the feedthrough in a same direction as the length of the metal plate is greater than 5 to 1; and
a hybrid circuit electrically coupled to vias of the feedthrough.

2. The device of claim 1, in which the metallic plate comprises a feature with reduced thickness that reduces lateral stresses transmitted from the metallic plate to the electrical feedthrough.

3. The device of claim 1, further comprising a compression braze joint, the compression braze joint forming a hermetic joint between the metallic plate and the ceramic feedthrough.

4. The device of claim 1, further comprising a metallic coating disposed on both sides of the vias to form connection pads.

5. The device of claim 4, in which the metallic coating on an interior side of the feedthrough is coated with a first metallic material and the exterior side of the feedthrough is coated with a second metallic material different from the first metallic material.

6. The device of claim 4, in which multiple vias each form an electrical connection between a single exterior connection pad and a single interior connection pad.

7. The device of claim 1, in which the feedthrough comprises a multilayered co-fired ceramic, in which the vias jog between layers of the multilayered co-fired ceramic material.

8. The device of claim 7, in which the vias pass linearly through at least two adjacent outer layers of the feedthrough and jog in central layers of the feedthrough.

9. The device of claim 7, in which at least one of the vias comprises a first conductive material forming an electrical path through an exterior layer of the feedthrough and a second conductive material forming an electrical path through interior layers of the feedthrough, the first conductive material and second conductive material being electrically joined and forming an electrically conductive path through the feedthrough.

10. The device of claim 1, in which a braze material is disposed between the metallic plate and a radial wall of the feedthrough.

11. The device of claim 1, in which a detachable connector is configured to attach to the feedthrough.

12. The device of claim 1, in which the ceramic feedthrough is recessed from an exterior surface of the metallic plate, the metallic plate including at least one groove, apart from an opening housing the feedthrough, configured to reduce stresses transferred through the metallic plate to the ceramic feedthrough.

13. The device of claim 1, in which the ceramic feedthrough is located within a radial wall of the hermetically sealed case.

14. The device of claim 13, in which hermetically sealed case comprises a plurality of ceramic feedthroughs, at least one of the plurality of ceramic feedthroughs being located within the radial wall of the hermetically sealed case.

15. A method for fabricating a device with a hermetic electrical feedthrough comprising:
   forming a metallic plate with an aperture, wherein a ratio of a diameter of the aperture to a diameter of the plate is less than 1 to 5;
   forming a multilayer ceramic feedthrough with electrical vias;
   forming connection pads on either side of the electrical vias;
   forming a hermetic joint which seals the ceramic feedthrough plate into the aperture; and
   electrically connecting a separate co-fired ceramic hybrid circuit to the ceramic feedthrough.

16. The method of claim 15, further comprising forming gold connection pads on the interior surface of the feedthrough and forming platinum connector pads on the exterior surface of the feedthrough, the connector pads being formed over the electrical vias.

17. The method of claim 15, in which attaching a ceramic hybrid circuit to the feedthrough comprises making a blind attachment between the ceramic hybrid circuit and connection pads on an interior surface of the feedthrough.

18. The method of claim 15, further comprising selecting composition of the feedthrough such that the feedthrough has a coefficient of thermal expansion which is lower than a coefficient of thermal expansion of the metallic plate and the braze material, the metallic plate being one of titanium and a titanium alloy; in which forming a hermetic joint comprises forming a compression braze joint.

19. The method of claim 18, in which forming a compression braze joint comprises:
   heating the feedthrough and the metallic plate above the melting point of a braze material, the braze material filing a gap between the feedthrough and the metallic plate; and
   reducing the temperature of the feedthrough and metallic plate such that the braze material solidifies and the metallic plate and braze material contract over the feedthrough to form a compression bond.

20. The method of claim 19, in which the electrical vias pass straight through two or more adjacent outer layers of the multilayered co-fired ceramic feedthrough and jog between central layers of the multilayered co-fired ceramic feedthrough.

21. The method of claim 15, in which the feedthrough comprises a multilayered co-fired ceramic.

22. A device comprising:
   a hermetically sealed case with electronic circuitry housed within; in which one surface of the hermetically sealed case comprises:
   a metallic plate;
   a co-fired ceramic electrical feedthrough comprising a number of vias being hermetically joined to the metallic plate, an exterior surface of the ceramic feedthrough being recessed relative to a surface on the metallic plate so as to protect the ceramic feedthrough from damage; and
   a hybrid circuit electrically coupled to vias of the feedthrough.

* * * * *